United States Patent
Wakita

(10) Patent No.: US 6,781,009 B2
(45) Date of Patent: Aug. 24, 2004

(54) METHOD FOR PRODUCING 4-CYANO-3-OXOBUTANOATE AND 4-CTANO-3-HYDROXYBUTANOATE

(75) Inventor: Ryuhei Wakita, Toyonaka (JP)

(73) Assignee: Sumitomo Chemical Company, Limited, Osaka (JP)

(*) Notice: Subject to any disclaimer, the term of this patent is extended or adjusted under 35 U.S.C. 154(b) by 25 days.

(21) Appl. No.: 09/984,334

(22) Filed: Oct. 29, 2001

(65) Prior Publication Data

US 2003/0105347 A1 Jun. 5, 2003

(30) Foreign Application Priority Data

Oct. 31, 2000 (JP) ........................................ 2000-332640
Dec. 7, 2000 (JP) ........................................ 2000-372705

(51) Int. Cl.[7] ............................................ C07C 255/17
(52) U.S. Cl. ..................................................... 558/442
(58) Field of Search .......................... 558/442; 546/321

(56) References Cited

FOREIGN PATENT DOCUMENTS

EP     0 573 184 A1    12/1993

OTHER PUBLICATIONS

Kellogg et al. Org. Chem. (1980), 45, 2854–2861.*
Troostwijk & Kellogg, "Method for the Synthesis of 4–Substituted Acetoacetates", J.C.S. Chem. Comm., 1997, (Dept. Of Organic Chemistry, Univ. of Groningen, Nijenborgh, Groningen, The Netherlands), pp. 932–933.

Itoh et al., "Production of Chiral Alcohols By Enantioselective Reduction With NADH–Dependent Phenylacetaldehyde Reductase From Corynebacterium Strain, ST–10", Journal of Molecular Catalysts B: Enzymatic 6 (1999) pp. 41–50.

Itho et al., "Purification and Characterization of Phenylacetaldehyde Reductase From A Styrene–Assimilating Corybacterium Strain, ST–10", Dept. of Applied Chemistry & Biotechnology, Faculty of Engineering, Fukui Univ., Japan, Applied & Environmental Microbiology, Oct. 1997, vol. 63, No. 10, pp. 3783–3787.

Wang et al., "Cloning, Sequence Analysis, and Expression in *Escherichia Coli* of the Gene Encoding Phenylacetaldehyde Reductase From Styrene–Assimilating Corynebacterium Sp. Strain ST–10", Applied Microbiology Biotechnology (1999) 52: 386–392.

* cited by examiner

*Primary Examiner*—Joseph K. McKane
*Assistant Examiner*—Rebecca Anderson
(74) *Attorney, Agent, or Firm*—Fitch, Even, Tabin & Flannery

(57) ABSTRACT

There are provided a method for producing a 4-cyano-3-oxobutanoate by reacting a 4-halo-3-oxobutanoate with an alkaline metal cyanide in methanol, a process for producing 4-cyano-3-hydroxybutanoate therefrom.

2 Claims, No Drawings

METHOD FOR PRODUCING 4-CYANO-3-OXOBUTANOATE AND 4-CTANO-3-HYDROXYBUTANOATE

FIELD OF THE INVENTION

The present invention relates to a method for producing 4-cyano-3-oxyobutanoate and a process for producing 4-cyano-3-hydroxybutanoate, which is a useful intermediate compound for the production of pharmaceuticals (for example, JP-A-5-331128).

BACKGROUND OF INVENTION

There has been disclosed a method for producing Ethyl 4-cyano-3-oxobutanoate by reacting ethyl 4-bromo-3-oxobutanoate with sodium hydride and reacting the resulting mixture with a cyanide ion in J. Chem. Soc. Chem. Comm. p932–933 (1977).

However, this method was not always satisfactory in that it requires tedious procedures as described above.

SUMMARY OF THE INVENTION

According to the present invention, 4-cyano-3-oxobutanoate can be readily obtained in an industrially improved process, and 4-cyano-3-hydroxybutanoate can also be readily obtained from 4-cyano-3-oxobutanoate.

The present invention provides:

1. a process for producing 4-cyano-3-oxobutanoate of formula (1):

(1)

wherein R denotes a C1–C8 alkyl group, which comprises reacting a 4-halo-3-oxobutanoate compound of formula (2):

(2)

wherein X and R are defined as described above, with an alkali metal cyanide in methanol;

2. 4-cyano-3-oxobutanoate of formula (1):

(1)

wherein R denotes a C1–C8 alkyl group, with the proviso that R is not an ethyl group; and 3. a process for producing 4-cyano-3-hydroxybutanoate of formula (3):

(3)

wherein R denotes a C1–C8 alkyl group, which comprises reacting 4-cyano-3-oxobutanoate of formula (1):

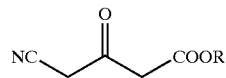

(1)

with an enzyme capable of converting 4-cyano-3-oxobutanoate of formula (1) to 4-cyano-3-hydroxybutanoate of formula (3), which enzyme has:

a) an amino acid sequence represented by SEQ ID NO:1, or b) an amino acid sequence wherein one to several amino acids in the amino acid sequence represented by SEQ ID NO:1 are deleted, substituted or added (the enzyme is referred to as "the present enzyme" hereinafter).

DETAILED DESCRIPTION

First, a description will be made to the process for producing 4-cyano-3-oxobutanoate of formula (1) as defined above, which comprises reacting a 4-halo-3-oxobutanoate compound of formula (2) as defined above, with an alkali metal cyanide in methanol.

Examples of the C1–C8 alkyl group represented by R in formulae (1) or (3) include, for example, a methyl group, an ethyl group, a propyl group, an isopropyl group, a n-butyl group, n-pentyl group, n-hexyl group, n-heptyl group, n-octyl group.

The halogen atom represented by X includes, for example, a chlorine atom and a bromine atom.

Examples of the alkali metal cyanide include, for example, sodium cyanide and potassium cyanide.

The amount of the alkali metal cyanide that may be used is usually 0.8 to 1.3 moles per mol of a 4-halo-3-oxobutanoate compound of formula (1).

The alkali metal cyanide and 4-halo-3-oxobutanoate of formula (2) may be respectively used as it is or as a methanol solution.

Any amount of methanol that can facilitate the reaction can be used in the present process, and is usually 3 to 10000 parts by weight per 1 part by weight of the compound of formula (2).

4-Halo-3-oxobutanoate of formula (2) and the alkali metal cyanide may be allowed to contact in a following manner. For example, (1) the 4-halo-3-oxobutanoate or a methanol solution thereof and the alkali metal cyanide or a methanol solution thereof are simultaneously added in a reactor; (2) to the 4-halo-3-oxobutanoate or a methanol solution thereof is added the alkali metal cyanide or a methanol solution thereof; or (3) the 4-halo-3-oxobutanoate or a methanol solution thereof is dropwise added to a solution of the alkali metal cyanide in methanol.

The reaction temperature is usually at a range of from −10° C. to the boiling temperature of reaction mixture, preferably at −10 to 40° C.

The progress of the reaction can be monitored by any conventional method such as high performance liquid chromatography, gas-chromatography, thin layer chromatography or the like. After completion of the reaction, the reaction mixture is subjected to usual post-treatment such as extraction with a water-immiscible organic solvent, concentration and/or the like, and the obtained product may be further purified by chromatography, recrystallization or distillation, if necessary.

Next, a description will be made to the process for producing 4-cyano-3-hydroxybutanoate of formula (3), which comprises reacting the 4-cyano-3-oxobutanoate (1) with the present enzyme.

In this process, 4-cyano-3-oxobutanoate is contacted with the present enzyme, thereby the carbonyl group at 3-position of the 4-cyano-3-oxobutanoate is reduced to give a corresponding hydroxy group at 3-position to produce optically active 4-cyano-3-hydroxybutanoate.

The reaction is usually carried out in the presence of water. The water may also be in a form of a buffer solution. Examples of the buffer solution to be used in this case include alkali metal salts of phosphoric acid such as sodium phosphate and potassium phosphate, and alkali metal salts of acetic acid such as sodium acetate and potassium acetate.

The reaction may be conducted within a pH range where the reaction is not adversely affected. It is usually conducted in the range of from pH 4 to pH 10.

When a buffer solution is used as a solvent, the amount thereof is usually not more than 100 parts by weight per 1 part by weight of the 4-cyano-3-oxobutanoate of formula (1).

The reaction temperature is usually from 0 to 70° C., preferably from 10 to 40° C.

The reaction can also be conducted in the presence of an organic solvent in addition to water. Examples of the organic solvent in this case include ethers such as tetrahydrofuran, t-butyl methyl ether and isopropyl ether, hydrocarbons such as toluene, hexane, cyclohexane, heptane, isooctane and decane, alcohols such as t-butanol, methanol, ethanol, isopropanol and n-butanol, sulfoxides such as dimethyl sulfoxide, ketones such as acetone, nitriles such as acetonitrile and mixtures thereof.

The amount of the solvent that may be used in the reaction is usually not more than 100 parts by weight, preferably not more than 50 parts by weight per 1 part by weight of the 4-cyanoacetoacetate compound of formula (1).

The reacting of the 4-cyano-3-oxobutanoate (1) with the present enzyme is preferably conducted in the co-presence of a co-enzyme (for example, NADH and/or NADPH). The amount of the co-enzyme that may be used in the reaction is usually not more than 0.5 part by weight, preferably not more than 0.1 part by weight per 1 part by weight of 4-cyano-3-oxobutanoate of formula (1).

Following compounds and dehydrogenases are more prefereably added in order to enhance the efficiency of the co-enzyme.

1) Compounds such as formic acid, glucose, isopropanol, 2-butanol, 2-pentanol, 2-hexanol, 2-heptanol, 2-octanol or the like.

The amount of these compounds that may be used is usually not more than 100 parts by weight, preferably not more than 10 parts by weight per 1 part by weight of 4-cyano-3-oxobutanoate of formula (1).

2) Dehydrogenases such as formic acid dehydrogenase, glucose dehydrogenase or the like.

The amount of the dehydrogenase that may be used is not more than 0.1 part by weight, preferably not more than 0.05 part by weight per 1 part by weight of 4-cyano-3-oxobutanoate of formula (1).

The reaction can be carried out by, for example, mixing water, 4-cyano-3-oxobutanoate of formula (1) and the present enzyme, and the co-enzyme and an organic solvent may be further added thereto, if desired, under stirring and shaking.

The progress of the reaction can be traced by monitoring the amount of the compound in the reaction solution by liquid chromatography, gas chromatography or the like. The reaction time usually ranges from 5 minutes to 4 days.

After the completion of the reaction, the product can be isolated, for example, by extracting the reaction solution with an organic solvent such as hexane, heptane, tert-butyl methyl ether, ethyl acetate and toluene, drying the organic layer, followed by concentration thereof. The product may be purified by column chromatography or the like, if necessary.

According the reduction process using the enzyme, the carbonyl group at 3-position of the 4-cyano-3-oxobutenoate of formula (2) is reduced to give a corresponding hydroxy compound (4-cyano-3-hydroxybutenoate of formula (3)), thereby optically active 4-cyano-3-hydroxybutenoate of formula (3) can be obtained.

Examples of the present enzyme include, for example, the enzyme having an amino acid sequence represented by SEQ ID NO: 1, and the enzyme having an amino acid sequence as depicted by SEQ ID NO: 1 wherein one to several amino acids are deleted, substituted, or added.

The present enzyme can be produced by culturing a microorganism containing a polynucleotide that encodes the present enzyme.

Examples of the polynucleotide include, for example, the polynucleotide represented by SEQ ID NO: 2 (Appl. Microbiol. Biotechnol (1999) 52, 386–392), and a polynucleotide coding for an amino acid sequence as depicted by SEQ ID NO: 1, wherein one to several amino acids are deleted, substituted, or added in the amino acid sequence of SEQ ID NO: 1.

The polynucleotide sequence coding for the amino acid sequence of the present enzyme may be either that naturally occurring or that resulting from variation treatment (a partial variation introducing method, a mutational treatment and the like) of a naturally occurring gene.

The present enzyme can be also produced, for example, by using a site-specific variation inducing method, a method comprising selectively cleaving the polynucleotide, subsequently removing or adding a selected nucleotide and then connecting the polynucleotide, or an oligonucleotide variation inducing method, these methods being well-known techniques for causing point variation or the like in a DNA, and subsequently performing the preparation of a transformant as described below.

The microorganism containing the desired polynucleotide as above can be produced by transfecting or transforming an appropriate microorganism host cell by a known manner.

Examples of the host cell that may be used to express the present polynucleotide such as the polynucleotide sequence represented by SEQ ID NO:2 include, for example, the cells of microorganisms belonging to Escherichia, Bacillus, Corynebacterium, Staphylococcus, Streptomyces, Saccharomyces, Kluyveromyces or Aspergillus.

Any conventional transforming or transfecting method for introducing the desired polynucleotide to the host cell may be used, depending upon the host cell. Examples thereof include, for example, a calcium chloride method disclosed, for example, in "Molecular Cloning: A Laboratory Manual $2^{nd}$ edition" (1989), Cold Spring Harbor Laboratory Press, "Current Protocols in Molecular Biology" (1987), John Wiley & Sons, Inc. ISBNO-471-50338-X, and an electroporation method disclosed, for example, in "Methods in Electroporation: Gene Pulser/E. coli Pulser System Bio-Rad Laboratories (1993)".

For example, a plasmid such as pUAR may be used to produce a transformed host cell. The plasmid was deposited under Butapest Treaty as FERM BP-7752, which had been originally deposited as FERM P-18127.

The microorganism, which are transfected or transformed with a vector containing the gene, can be selected using, as an indicator, a phenotype of a selected marker gene contained in a vector as described below. Whether a transformed microorganism is expressing the gene or not can be examined by preparing a vector DNA from the transformed microorganism and performing, for the DNA prepared, the conventional methods (for example, checking of a restricted enzyme site, analysis of base sequences and Southern hybridization) disclosed, for example, in J. Sambrook et al., Molecular Cloning, Cold Spring Harbor (1989).

Culturing the transfected or transformed microorganism, which contains a polynucleotide coding for the present enzyme such as a gene represented by SEQ ID NO:2 or the like, is conducted, for example, by using a suitable medium, carbon source, nitrogen source, in the following manner.

Examples of the medium for culturing the microorganism include, for example, various kinds of mediums, which adequately contain suitable carbon sources, nitrogen sources, organic salts, inorganic salts or the like.

Examples of the carbon sources include, for example, saccharides such as glucose, dextrin and sucrose, sugar alcohols such as glycerol, organic acids such as fumaric acid, citric acid and pyruvic acid, animal or vegetable oils, molasses and the like. It is usually recommended to add such carbon sources to a culturing medium in an amount of about 0.1 to 20%(w/v) relative to the whole medium.

Examples of the nitrogen sources include, for example, naturally occurring organic nitrogen sources and amino acids such as meat extract, peptone, yeast extract, malt extract, soybean flour, corn steep liquor, cotton seed flour, dry yeast and casamino acid, ammonium salts of inorganic acids or nitrates such as sodium nitrate, ammonium chloride, ammonium sulfate and ammonium phosphate, ammonium salts of organic acids such as ammonium fumarate and ammonium citrate, organic or inorganic nitrogen sources such as urea. Among them, the ammonium salts of organic acids, the naturally occurring nitrogen sources and the amino acids can also be used as carbon sources in many cases. Nitrogen sources in an amount of about 0.1 to 30%(w/v) relative to the whole culturing medium are preferably added.

Examples of the organic or inorganic salts include, for example, chlorides, sulfates, acetates, carbonates and phosphates of potassium, sodium, magnesium, iron, manganese, cobalt, zinc and so on, and specifically, sodium chloride, potassium chloride, magnesium sulfate, ferrous sulfate, manganese sulfate, cobalt chloride, zinc sulfate, copper sulfate, sodium acetate, calcium carbonate, sodium carbonate, potassium dihydrogen phosphate, dipotassium hydrogen phosphate and the like. It is usually recommended to add such organic or inorganic salts in an amount of about 0.00001 to 5%(w/v) relative to the whole culturing medium.

Furthermore, a small amount of isopropyl thio-β-D-galactoside (IPTG), as an inducer for inducing the production of the enzyme, may be added to a medium for cultivating a host cell introduced with a gene comprising a promoter such as tac-promoter, trc-promoter or lac-promoter, which is induced by allolactose, and a gene for coding the present enzyme, both of which are functionally linked.

The cultivating can be performed according to the methods usually employed for cultivating microorganisms. For example, liquid culture such as shaking culture in test tube, reciprocal shaking culture, jar fermenter culture and tank culture and solid culture are possible. When a jar fermenter is used, sterile air must be introduced into the jar fermenter and a usually applied aeration condition is about 0.1 to about 2 times the volume of culture medium per minute. The cultivating temperature may adequately be changed within a range in which the microorganism can grow, and preferred cultivating temperature is in the range of from about 35° C. to about 42° C. are preferable. The culture medium desirably has pH within about 6 to about 8. While the cultivating time varies with culture conditions, preferred is usually from about 1 day to about 5 days.

For the production process of the present invention, for example, cells containing the present enzyme obtained in the above-mentioned procedure, treated cells, or the purified enzyme can be used.

Examples of the treated cells include freeze dried cells, organic solvent-treated cells, dried cells, disrupted cells, self-digested cells, supersonic-treated cells, cell extract and alkali-treated cells. Furthermore, those obtained by fixing the above-mentioned cells by the procedures conventionally employed are also mentioned.

The purified enzyme can be produced in the present invention by, for example, purifying the present enzyme from cultured microorganisms expressing the present enzyme.

The method for purifying the present enzyme from cultured microorganisms expressing the present enzyme includes, for example, the following methods.

The present enzyme can be obtained by the following manner. Cells are collected first from cultured microorganisms by centrifugal separation or the like and then are crushed by physically disrupting methods such as supersonic treatment, dynomill treatment and French press treatment, chemically disrupting methods using surfactants or lytic enzymes such as lysozyme, or the like.

The present enzyme can be purified by removing insolubles from the resulting disrupted cell solution by centrifugal separation, membrane filter filtration or the like to prepare a cell-free extract and subsequently subjecting the extract to fractioning by suitable separation and purification methods such as cation exchange chromatography, anion exchange chromatography, hydrophobic chromatography, gel chromatography and the like.

In the chromatography, a support such as resin support (e.g., cellulose in which a carboxymethyl (CM) group, a DEAE group, a phenyl group or a butyl group has been introduced, dextran and agarose) can be used. Commercially available support-filled columns may also be used, and examples of which include, for example, Q-Sepharose FF, Phenyl Sepharose HP (Trademark, manufactured by Amersham Pharmacia Biotech K.K.) and TSK-gel G3000SW (Trademark name, manufactured by Tosoh Corporation).

EXAMPLES

The present invention is further described in the following examples, which are not intended to restrict the invention.

In the following description, the purity of a synthesized compound is based on the % area of the peak of a gas chromatogram.

Example 1

10.0 g of potassium cyanide was dissolved in 400 ml of methanol, to which then 24.8 g of methyl 4-bromo-3-oxobutanoate was added dropwise from a dropping funnel over 20 minutes. Methyl 4-bromo-3-oxobutanoate remaining in the dripping funnel was dissolved further in 10 ml of methanol and added dropwise, and the mixture was stirred with cooling on ice for 1 hour and at room temperature for 2 hours. Subsequently, the reaction mixture was cooled on ice, and treated dropwise with 3 ml of a concentrated hydrochloric acid. The reaction mixture was extracted three times with diethylether (2000 ml of diethylether in total). The organic layers were combined, washed twice with 100 ml of saturated brine, dried over magnesium sulfate, concentrated under reduced pressure to obtain 15.3 g of methyl 4-cyano-3-oxobutanoate (purity: 83%).

GC Conditions

Column: DB-1 (0.25 mm in inner diameter×30 mm in length, particle size: 0.25 μm)

Injection temperature: 250° C.

Detector: FID (300° C.)

Chamber temperature: 50° C. for 5 minutes, raising by 5° C. per minutes to 250° C. which is kept for 10 minutes Carrier gas: 1.0 ml/minute Split ratio: 1/10

Mass spectrum: 141.0 (EI) $^3$H-NMR(CDCl$_3$) δ(ppm):2.47 (1H), 3.86(3H), 4.43(2H), 6.71(1H)

Example 2

Each 4-cyano-3-oxobutanoate was obtained similarly to Example 1 except for using respective compound indicated in the table instead of methyl 4-bromo-3-oxobutanoate as a starting compound. The results are shown in Table 1.

TABLE 1

| Starting compound | Synthesized compound | Starting material (g) | Yield (g) | Purity |
|---|---|---|---|---|
| Ethyl 4-bromo-3-oxo-butanoate | Ethyl 4-cyano-3-oxo-butanoate | 20.9 | 14.0 | 63% |
| Isopropyl 4-bromo-3-oxo-butanoate | Isopropyl 4-cyano-3-oxo-butanoate | 18.8 | 13.5 | 72% |
| Octyl 4-bromo-3-oxo-butanoate | Octyl 4-cyano-3-oxo-butanoate | 17.2 | 14.5 | 39% |

Example 3

10 g of methyl 4-bromo-3-oxobutanoate is dissolved in 100 g of methanol. The resultant solution is cooled to 0° C. and a solution of 4 g of sodium cyanide in 100 g of methanol is added thereto. After completion of the addition, the mixture is warmed gradually to room temperature under stirring. Thereafter, the reaction mixture is poured into water, and extracted with ethyl acetate. The organic layer is washed with saturated brine, dried, concentrated to obtain methyl 4-cyano-3-oxobutanoate.

Example 4

After 0.4 g of potassium cyanide was added at room temperature to a solution of 1 g of Methyl 4-chloro-3-oxobutanoate in 20 ml of methanol, the resulting mixture was warmed to 40° C. and maintained for further 8 hours. Thereafter, reaction solution was cooled and pH of the solution was adjusted to 3 by adding 10 ml of water and a few drops of concentrated sulfuric acid. After the mixture was extracted thrice with diethyl ether, total amount of which was 100 ml, the separated organic layers were combined and concentrated under reduced pressure to give 0.6 g of methyl 4-cyano-3-oxobutanoate (Purity: 71%).

Example 5

In a flask, 900 ml of a liquid medium, which was obtained by dissolving 10 g of tripton, 5 g of yeast extract and 5 g of sodium chloride in 1000 ml of water and then adjusting to pH 7.0 by dropping a 1N aqueous sodium hydroxide solution, was charged and then sterilized. Subsequently, ampicillin and isopropyl thio-β-D-galactoside (IPTG) were added so that their concentrations became 100 μg/ml and 0.4 mM, respectively. To the resulting medium was seeded 1 ml of a culture solution resulting from the cultivation, in a liquid medium having the above-mentioned composition, of a transformant *E. coli* JM109/pUAR strain obtained by the transformation of *E. coli* JM109 strain in the usual procedure using a plasmid pUAR (accession number: FERM BP-7752, which was transferred from FERM P-18127) containing a DNA represented by SEQ ID NO:2. The resultant was cultured under shaking at 37° C. for 14 hours. The cells obtained by centrifugal separation (15000×g, 15 minutes, 4° C.) of the above culture solution were suspended in 30 ml of a 50 mM potassium dihydrogen phosphate-dipotassium hydrogen phosphate buffer solution (pH 7.0) and the resulting suspension was centrifugally separated (15000×g, 15 minutes, 4° C.), resulting in washed cells.

Twenty one milligrams of ethyl 4-cyano-3-oxobutanoate and 1 ml of a 50 mM potassium dihydrogen phosphate-dipotassium hydrogen phosphate buffer solution (pH 7.0) were mixed and 75 μl of isopropanol and 1.5 ml of decane were added thereto. To the resultant, a suspension resulting from suspending 200 mg of the above-mentioned washed cells in 0.5 ml of a potassium dihydrogen phosphate-dipotassium hydrogen phosphate buffer solution (pH 7.0) was poured and was stirred for 24 hours. Subsequently, 3 ml of ethyl acetate was added to the reaction solution and was stirred violently. This solution was separated by centrifugation (3500 rpm, 10 minutes) and the resulting organic layer was subjected to gas chromatography analysis. The agreement in retention time with a standard ethyl 4-cyanoacetoacetate and the mass spectrum data obtained confirmed that ethyl 4-cyano-3-hydroxybuanoate.

MS: (m/z) 157 (M$^+$), 130, 117, 112

Gas Chromatography Analysis Conditions:

Column: DB-1 (manufactured by J & W Science Co., Ltd.) 0.53 mmφ×30 m, membrane thickness 1.5 μm Inlet temperature: 120° C.

Column chamber temperature: 50° C.→(4° C.)→170° C.

FID detector temperature: 300° C.

Carrier gas: Helium

Flow rate: 10 ml/min

Retention time of ethyl 4-cyano-3-hydroxybuanoate: 14 minutes

What is claimed is:

1. Methyl 4-cyano-3-oxobutanoate.

2. Isopropyl 4-cyano-3-oxobutanoate.

* * * * *

SEQUENCE LISTING

<160> NUMBER OF SEQ ID NOS: 2

<210> SEQ ID NO 1
<211> LENGTH: 385
<212> TYPE: PRT
<213> ORGANISM: Corynebacterium sp.

<400> SEQUENCE: 1

```
Met Lys Ala Ile Gln Tyr Thr Arg Ile Gly Ala Pro Glu Leu Thr
 1               5                  10                  15

Glu Ile Pro Lys Pro Glu Pro Gly Pro Gly Val Leu Leu Glu Val
                 20                  25                  30

Thr Ala Ala Gly Val Cys His Ser Asp Asp Phe Ile Met Ser Leu Pro
             35                  40                  45

Glu Glu Gln Tyr Thr Tyr Gly Leu Pro Leu Thr Leu Gly His Glu Gly
             50                  55                  60

Ala Gly Lys Val Ala Ala Val Gly Glu Gly Val Glu Gly Leu Asp Ile
 65                  70                  75                  80

Gly Thr Asn Val Val Val Tyr Gly Pro Trp Gly Cys Gly Asn Cys Trp
                 85                  90                  95

His Cys Ser Gln Gly Leu Glu Asn Tyr Cys Ser Arg Ala Gln Glu Leu
                100                 105                 110

Gly Ile Asn Pro Pro Gly Leu Gly Ala Pro Gly Ala Leu Ala Glu Phe
            115                 120                 125

Met Ile Val Asp Ser Pro Arg His Leu Val Pro Ile Gly Asp Leu Asp
            130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ser Tyr Ala Val
                165                 170                 175

Val Ile Gly Thr Gly Gly Leu Gly His Val Ala Ile Gln Leu Leu Arg
                180                 185                 190

His Leu Ser Ala Ala Thr Val Ile Ala Leu Asp Val Ser Ala Asp Lys
            195                 200                 205

Leu Glu Leu Ala Thr Lys Val Gly Ala His Glu Val Val Leu Ser Asp
            210                 215                 220

Lys Asp Ala Ala Glu Asn Val Arg Lys Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
                260                 265                 270

Asp Gly Gln Ala His Ala Lys Val Gly Phe Phe Gln Ser Pro Tyr Glu
            275                 280                 285

Ala Ser Val Thr Val Pro Tyr Trp Gly Ala Arg Asn Glu Leu Ile Glu
            290                 295                 300

Leu Ile Asp Leu Ala His Ala Gly Ile Phe Asp Ile Gly Gly Gly Asp
305                 310                 315                 320

Leu Gln Ser Arg Gln Arg Cys Arg Ser Val Ser Thr Gly Cys Arg
                325                 330                 335

Asn Ala Gln Arg Pro Cys Gly Cys Gly Pro Trp Ser Val Val Pro Thr
            340                 345                 350

Ala Val Glu Arg Gln Arg Lys Asn Thr Asp Ala Arg Pro Asn Ser Ile
```

```
              355                 360                 365
Arg Pro Gly Ile Ser Val Arg Asn Ser Val Cys Ala Ser Cys Thr Pro
    370                 375                 380

Arg
385

<210> SEQ ID NO 2
<211> LENGTH: 1158
<212> TYPE: DNA
<213> ORGANISM: Corynebacterium sp.
<220> FEATURE:
<221> NAME/KEY: CDS
<222> LOCATION: (1)..(1158)

<400> SEQUENCE: 2 atg aag gcg atc cag tac acg cga atc ggc gcg gaa ccc gaa ctc acg       48
Met Lys Ala Ile Gln Tyr Thr Arg Ile Gly Ala Glu Pro Glu Leu Thr
 1               5                  10                  15 gag att ccc aaa ccc gag ccc ggt cca ggt gaa gtg ctc ctg gaa gtc       96
Glu Ile Pro Lys Pro Glu Pro Gly Pro Gly Glu Val Leu Leu Glu Val
                20                  25                  30 acc gct gct ggc gtc tgc cac tcg gac gac ttc atc atg agc ctg ccc      144
Thr Ala Ala Gly Val Cys His Ser Asp Asp Phe Ile Met Ser Leu Pro
            35                  40                  45 gaa gag cag tac acc tac ggc ctt ccg ctc acg ctc ggc cac gaa ggc      192
Glu Glu Gln Tyr Thr Tyr Gly Leu Pro Leu Thr Leu Gly His Glu Gly
         50                  55                  60 gca ggc aag gtc gcc gcc gtc ggc gag ggt gtc gaa ggt ctc gac atc      240
Ala Gly Lys Val Ala Ala Val Gly Glu Gly Val Glu Gly Leu Asp Ile
 65                  70                  75                  80 gga acc aat gtc gtc gtc tac ggg cct tgg ggt tgc ggc aac tgt tgg      288
Gly Thr Asn Val Val Val Tyr Gly Pro Trp Gly Cys Gly Asn Cys Trp
                 85                  90                  95 cac tgc tca caa gga ctc gag aac tat tgc tct cgc gcc caa gaa ctc      336
His Cys Ser Gln Gly Leu Glu Asn Tyr Cys Ser Arg Ala Gln Glu Leu
            100                 105                 110 gga atc aat cct ccc ggt ctc ggt gca ccc ggc gcg ttg gcc gag ttc      384
Gly Ile Asn Pro Pro Gly Leu Gly Ala Pro Gly Ala Leu Ala Glu Phe
        115                 120                 125 atg atc gtc gat tct cct cgc cac ctt gtc ccg atc ggt gac ctc gac      432
Met Ile Val Asp Ser Pro Arg His Leu Val Pro Ile Gly Asp Leu Asp
    130                 135                 140 ccg gtc aag acg gtg ccg ctg acc gac gcc ggt ctg acg ccg tat cac      480
Pro Val Lys Thr Val Pro Leu Thr Asp Ala Gly Leu Thr Pro Tyr His
145                 150                 155                 160 gcg atc aag cgt tct ctg ccg aaa ctt cgc gga ggc tcg tac gcg gtt      528
Ala Ile Lys Arg Ser Leu Pro Lys Leu Arg Gly Gly Ser Tyr Ala Val
                165                 170                 175 gtc att ggt acc ggc ggt ctc ggc cac gtc gct att cag ctc ctc cgc      576
Val Ile Gly Thr Gly Gly Leu Gly His Val Ala Ile Gln Leu Leu Arg
            180                 185                 190 cac ctc tcg gcg gca acg gtc atc gct ttg gac gtg agc gcg gac aag      624
His Leu Ser Ala Ala Thr Val Ile Ala Leu Asp Val Ser Ala Asp Lys
        195                 200                 205 ctc gaa ctg gca acc aag gta ggc gct cac gaa gtg gtt ctg tcc gac      672
Leu Glu Leu Ala Thr Lys Val Gly Ala His Glu Val Val Leu Ser Asp
    210                 215                 220 aag gac gcg gcc gag aac gtc cgc aag atc act gga agt caa ggc gcc      720
Lys Asp Ala Ala Glu Asn Val Arg Lys Ile Thr Gly Ser Gln Gly Ala
225                 230                 235                 240
```

```
gca ttg gtt ctc gac ttc gtc ggc tac cag ccc acc atc gac acc gcg    768
Ala Leu Val Leu Asp Phe Val Gly Tyr Gln Pro Thr Ile Asp Thr Ala
            245                 250                 255 atg gct gtc gcc ggc gtc gga tca gac gtc acg atc gtc ggg atc ggg    816
Met Ala Val Ala Gly Val Gly Ser Asp Val Thr Ile Val Gly Ile Gly
            260                 265                 270 gac ggc cag gcc cac gcc aaa gtc ggg ttc ttc caa agt cct tac gag    864
Asp Gly Gln Ala His Ala Lys Val Gly Phe Phe Gln Ser Pro Tyr Glu
            275                 280                 285 gct tcg gtg aca gtt ccg tat tgg ggt gcc cgc aac gag ttg atc gaa    912
Ala Ser Val Thr Val Pro Tyr Trp Gly Ala Arg Asn Glu Leu Ile Glu
            290                 295                 300 ttg atc gac ctc gcc cac gcc ggc atc ttc gac atc ggc ggt gga gac    960
Leu Ile Asp Leu Ala His Ala Gly Ile Phe Asp Ile Gly Gly Gly Asp
305                 310                 315                 320 ctt cag tct cga caa cgg tgc cga agc gta tcg act act ggc tgc cgg   1008
Leu Gln Ser Arg Gln Arg Cys Arg Ser Val Ser Thr Thr Gly Cys Arg
                325                 330                 335 aac gct cag cgg ccg tgc ggt tgt ggt ccc tgg tct gta gta ccg aca   1056
Asn Ala Gln Arg Pro Cys Gly Cys Gly Pro Trp Ser Val Val Pro Thr
            340                 345                 350 gcg gta gaa cga cag cgg aaa aac act gat gcc cgg ccg aat tcg att   1104
Ala Val Glu Arg Gln Arg Lys Asn Thr Asp Ala Arg Pro Asn Ser Ile
            355                 360                 365 cgg ccg ggc atc agt gtc aga aat tcg gtg tgc gct agc tgc acg cct   1152
Arg Pro Gly Ile Ser Val Arg Asn Ser Val Cys Ala Ser Cys Thr Pro
            370                 375                 380 cga tga                                                            1158
Arg
385
```